US006582713B2

(12) United States Patent
Newell et al.

(10) Patent No.: US 6,582,713 B2
(45) Date of Patent: Jun. 24, 2003

(54) COMPOSITIONS AND METHODS FOR PROMOTING WOUND HEALING

(75) Inventors: Martha K. Newell, Colorado Springs, CO (US); Ian Askill, Colorado Springs, CO (US); Javin Pierce, Stowe, VT (US); William Crisp, Paradise Valley, AZ (US)

(73) Assignees: Univ. of Colorado - Colorado Springs, Colorado Springs, CO (US); Medlogic Global Corp., Devon (GB); Anodose Dermal Product, Inc., Stowe, VT (US)

( * ) Notice: Subject to any disclaimer, the term of this patent is extended or adjusted under 35 U.S.C. 154(b) by 0 days.

(21) Appl. No.: 09/823,851

(22) Filed: Mar. 30, 2001

(65) Prior Publication Data

US 2002/0122787 A1 Sep. 5, 2002

Related U.S. Application Data (60) Provisional application No. 60/195,580, filed on Apr. 6, 2000.

(51) Int. Cl.[7] .................. A61K 33/38; A61K 38/28; A61K 47/32; A61L 26/00
(52) U.S. Cl. ............... 424/407; 106/15.05; 424/443; 424/487; 424/618; 514/3; 514/4; 602/48; 602/50; 604/20; 604/304; 604/307; 607/50
(58) Field of Search ................ 514/3, 4; 424/405, 424/407, 409, 443, 487, 618, 619; 106/15.05, 155.2; 602/43, 48, 50, 52, 54; 604/20, 21, 304, 307; 607/50

(56) References Cited

U.S. PATENT DOCUMENTS

| | | | |
|---|---|---|---|
| 3,800,792 A | 4/1974 | McKnight et al. ............. | 602/50 |
| 4,528,265 A | 7/1985 | Becker ..................... | 435/172.1 |
| 4,847,049 A | 7/1989 | Yamamoto ................... | 422/424 |

(List continued on next page.)

FOREIGN PATENT DOCUMENTS

| | | |
|---|---|---|
| EP | 0 144 741 A1 | 6/1985 |
| JP | 20286176 A * | 11/1990 |
| WO | WO 94/15590 A1 | 7/1994 |

(List continued on next page.)

OTHER PUBLICATIONS

Alderson, M.R. et al., "Fas Transduces Activation Signals in Normal Human T Lymphocytes", *J. Exp. Med.*, Dec. 1993, pp. 2231–2235, vol. 178, The Rockefeller University Press.

Alderson, M.R. et al., "Regulation of apoptosis and T cell activation by Fas–specific mAb", *International Immunology*, 1994, pp. 1799–1806, vol. 6, No. 11, Oxford University Press.

(List continued on next page.)

*Primary Examiner*—Jeffrey E. Russel
(74) *Attorney, Agent, or Firm*—Wolf, Greenfield & Sacks PC (57) ABSTRACT

The present invention provides methods and compositions for promoting wound healing and reducing scar formation. In particular, the present invention provides cyanoacrylate polymer sealants formulated to contain biologically active elemental silver and/or insulin. The invention also provides methods and compositions for delivering silver and/or insulin in combination with cyanoacrylate sealants. In particular, the present invention provides methods and compositions suitable for treatment of wounds in diabetics, normal patients and surgical patients.

29 Claims, 1 Drawing Sheet

U.S. PATENT DOCUMENTS

| | | | |
|---|---|---|---|
| 4,913,908 A | 4/1990 | Couvreur et al. | 424/501 |
| 5,145,679 A | 9/1992 | Hinson | 424/401 |
| 5,328,687 A | 7/1994 | Leung et al. | 424/78.35 |
| 5,518,730 A | 5/1996 | Fuisz | 424/426 |
| 5,591,709 A | 1/1997 | Lindenbaum | 514/4 |
| 5,641,515 A | 6/1997 | Ramtoola | 424/490 |
| 5,654,267 A | 8/1997 | Vuori et al. | 514/2 |
| 5,684,042 A | 11/1997 | Greff et al. | 514/527 |
| 5,753,699 A | 5/1998 | Greff et al. | 514/527 |
| 5,785,972 A | 7/1998 | Tyler | 424/195.1 |
| 5,814,094 A | 9/1998 | Becker et al. | 607/50 |
| 5,902,594 A | 5/1999 | Greff et al. | 424/405 |
| 5,962,010 A | 10/1999 | Greff et al. | 424/443 |
| 6,001,345 A | 12/1999 | Askill et al. | 424/78.25 |
| 6,102,205 A | 8/2000 | Greff et al. | 424/78.25 |
| 6,129,696 A | 10/2000 | Sibalis | 604/20 |

FOREIGN PATENT DOCUMENTS

| | | |
|---|---|---|
| WO | WO 96/31231 A1 | 10/1996 |
| WO | WO 97/42940 A1 | 11/1997 |
| WO | WO 98/30091 A1 | 7/1998 |
| WO | WO 98/30092 A1 | 7/1998 |
| WO | WO 99/22934 A1 | 5/1999 |
| WO | WO 99/23150 A1 | 5/1999 |
| WO | WO 99/42535 A1 | 8/1999 |
| WO | WO 99/43359 A1 | 9/1999 |
| WO | WO 99/55374 A1 | 11/1999 |
| WO | PCT/US01/10245 | 3/2001 |

OTHER PUBLICATIONS

Bhushan, A. et al., "Drug resistance results in alterations in expression of immune recognition molecules and failure to express Fas (CD95)", *Immunology and Cell Biology*, 1998, pp. 350–356, vol. 76.

Bonduelle, S. et al., "Association of cyclosporin to isohexylcyanoacrylate nanospheres and subsequent release in human plasma in vitro", *J. Microencapsulation*, 1992, pp. 173–182, vol. 9, No. 2, Taylor & Ffrancis Ltd.

Chien, M.M. et al., "Fas–induced B Cell Apoptosis Required an Increase in Free Cytosolic Magnesium as an Early Event", *The Journal of Biological Chemistry*, Mar. 12, 1999, pp. 7059–7066, vol. 274, No. 11, The American Society for Biochemistry and Molecular Biology, Inc.

Couvreur, P., "Polyalkylcyanoacrylates as Colloidal Drug Carriers", *CRC Critical Reviews in Therapeutic Drug Carrier Systems*, 1988, pp. 1–20, vol. 5, No. 1.

Desbarats, J. et al., "Fas (CD95) expression and death–mediating function are induced by CD4 cross–linking on CD4+ T cells", *Proc. Acad. Sci. USA*, Oct. 1996, pp. 11014–11018, vol. 93.

Desbarats, J. et al., "Newly discovered role for Fas ligand in the cell–cycle arrest of CD4+ T cells", *Nature Medicine*, Dec. 1998, pp. 1377–1382, vol. 4, No. 12.

Desbarats, J. et al., "Dichotomy between naïve and memory CD4+ T cell responses to Fas engagement", *Proc. Natl. Acad. Aci. USA*, Jul. 1999, pp. 8104–8109, vol. 96.

Edmonds, T., "Evaluation of the effects of Topical Insulin on wound–healing in the distal limb of the horse", *Veterinary Medicine/Small Animal Clinician*, Apr. 1976, pp. 451–457.

Fung, M.C. et al., "Colloidal Silver Proteins Marketed as Health Supplements", *J. Amer. Med. Assoc.*, Oct. 18, 1995, pp. 1196–1197, vol. 274, No. 15.

Fung, M.C. et al., "Silver Products for Medical Indications: Risk–Benefit Assessment", *Clinical Toxicology*, 1996, pp. 119–126, vol. 34, No. 1, Marcel Dekker, Inc.

Gerber, R.M. et al., "Topical Application of Insulin in Decubitus Ulcers", *Nursing Research*, Jan.–Feb. 1979, pp. 16–19, vol. 28, No. 1.

Glasser, J. et al., "Diabetic Wound Healing and the Case for Supplemental Treatment with Topical Insulin", *The Journal of Foot Surgery*, 1982, pp. 117–121, vol. 21, No. 2.

Hanam, S.R. et al., "The Effect of Topical Insulin on Infected Cutaneous Ulcerations in Diabetic and Nondiabetic Mice", *The Journal of Foot Surgery*, 1983, pp. 298–301, vol. 22, No. 4.

Hennessey, P.J. et al., "Growth Factors and Diabetic Wound Healing: Epidermal Growth Factor and Insulin", *Current Surgery*, Jul.–Aug. 1989, pp. 285–286.

Huber, S.A. et al., "Hormonal Regulation of CD4+ T–Cell Responses in Coxsackievirus B3–Induced Myocarditis in Mice", *Journal of Virology*, Jun. 1999, pp. 4689–4695, vol. 73, No. 6, American Society for Microbiology.

Huber, S.A et al., "γδ+ T Cells Regulate Major Histocompatibility Complex Class II (1A and 1E)–Dependent Susceptibility to Coxsackievirus B3–Induced Autoimmune Myocarditis", *Journal of Virology*, Jul. 1999, pp. 5630–5636, vol. 73, No. 7, American Society for Microbiology.

Martin, P., "Wound Healing—Aiming for Perfect Skin Regeneration", *Science*, Apr. 4, 1997, pp. 75–81, vol. 276.

McCauley, R.L. et al., "Cytoprotection of Human Dermal Fibroblasts against Silver Sulfadiazine Using Recombinant Growth Factors", *Journal of Surgical Research*, 1994, pp. 378–384, vol. 56, Academic Press, Inc.

"Arglaes Antimicrobial Barrier Film Dressings", and "Advanced Wound Care: A Complete Reference of Products, Procedures & Services from Medline", Medline Industries, Inc., p. 4. www.medline.net (1999).

Newell, M.K. et al., "Does the Oxidative/Glycolytic Ratio Determine Proliferation or Death in Immune Recognition", *Annals. NY Academy of Sciences*, 1999, pp. 77–82, vol. 887.

Newell, M.K. et al., "Fas ligand: receptor or ligand?", *Apoptosis*, Oct. 1999, pp. 311–315, vol. 4, No. 5.

Owen–Schaub, L.B. et al., "Fas/APO–1 Expression and Function on Malignant Cells of Hematologic and Nonhematologic Origin", *Journal of Immunotherapy*, 1993, pp. 234–241, vol. 14, No. 3, Raven Press Ltd.

Owen,Schaub, L.B. et al., "Anti–Fas on Nonhematopoietic Tumors: Levels of Fas/APO–1 and bcl–2 Are Not Predictive of Biological Responsiveness", *Cancer Research*, Mar. 15, 1994, pp. 1580–1586, vol. 54.

Pierre, E.J. et al., "Effects of Insulin on Wound Healing", *The Journal of Trauma: Injury, Infection, and Critical Care*, 1998, pp. 342–345, vol. 44, No. 2, Williams & Wilkins.

Radwan, M.A et al., "In vivo performance of parenteral theophylline–loaded polyisobutylcyanoacrylate nanoparticles in rats", *European Journal of Pharmaceutical Sciences*, 1999, pp. 95–98, vol. 8, Elsevier Science B.V.

Rosenberg, C.S., "Wound Healing in the Patient with Diabetes Mellitus", *Nursing Clinics of North America*, Mar. 1990, pp. 247–261, vol. 25, No. 1.

Rund, C.R., "Non–conventional topical therapies for wound care", *Ostomy/Wound Management*, Jun. 1996, pp. 18–24, vol. 42, No. 5.

Servold, S.A., "Grown Factor Impact on Wound Healing", *Clinics in Podiatric Medicine and Surgery*, 1991, pp. 937–953, vol. 8, No. 4.

Shenk, J.S. et al., "Tobramycin–Adhesive in Preventing and Treating PTFE Vascular Graft Infections", *Journal of Surgical Research*, 1989, pp. 487–492, vol. 47, Academic Press, Inc.

Suzuki, I. et al., "Maximal Proliferation of Cytotoxic T Lymphocytes Requires Reverse Signaling through Fas Ligand", *J. Exp. Med.*, Jan. 5, 1998, pp. 123–128, vol. 187, No. 1, The Rockefeller University Press.

Van Ort, S.R. et al., "Topical Application of Insulin in the Treatment of Decubitus Ulcers: A Pilot Study", *Nursing Research*, Jan.–Feb. 1976, pp. 9–12, vol. 25, No. 1.

Verdun, C. et al., "Tissue distribution of doxorubicin associated with polyisohexylcyanoacrylate nonoparticles", *Cancer Chemotherapy and Pharmacology*, 1990, pp. 13–18, vol. 26.

Youssef, M. et al., "Effectiveness of Nanoparticle–Bound Ampicillin in the Treatment of *Listeria Monocytogenes* Infection in Athymic Nude Mice", *Antimicrobial Agents and Chemotherapy*, Aug. 1988, pp. 1204–1207, vol. 32, No. 8, American Society for Microbiology.

\* cited by examiner

FIGURE 1

Figure 1. Cyanoacrylate structure

COMPOSITIONS AND METHODS FOR PROMOTING WOUND HEALING

RELATED APPLICATIONS

This application claims priority under 35 U.S.C. §119 to U.S. Provisional patent application No. 60/195,580 filed on Apr. 6, 2000, the entire contents of which is hereby incorporated by reference.

GOVERNMENT SUPPORT

The present invention was supported in part by a grant from the United States Government National Institutes of Health under contract/grant no. R01GM62562. The U.S. Government may retain certain rights in the invention.

FIELD OF THE INVENTION

The invention relates to methods and compositions for promoting wound healing. In particular, the invention provides cyanoacrylate polymer sealants in combination with biologically active agents including silver and insulin.

BACKGROUND OF THE INVENTION

Normal wound healing involves the complex orchestration of a series of interrelated cellular events and cytokine cascades (Pierce, G. F. and Mustoe, T. A., Ann. Rev. Med., 46:467–481 (1995); and Martin, P., Science, 276:75–81 (1997)). The principle phases of wound healing consist of formation of a fibrin clot, followed by infiltration with inflammatory cells and fibroblasts, generation of granulation tissue and angiogenesis, wound contraction, and re-epithelialization. Growth factors and cytokines are supplied first by degranulating platelets, and later by fibroblasts and inflammatory cells, principally neutrophils and macrophages. The inflammatory response plays an active part in wound healing. If macrophage infiltration is prevented, wound healing is seriously impaired.

Currently, there are numerous methods and compositions available to treat wounds and to promote wound healing. A wound may constitute a variety of insults or damage to external body tissues, for example, a wound may involve a laceration, cut or scrape, surgical incision, sore, thermal burn, puncture, or decubitus ulcer, e.g., bed sores. Wounds can be classified in one of two general categories, partial thickness wounds or full thickness wounds. A partial thickness wound is limited to the epidermis and superficial dermis with no damage to the dermal blood vessels. A full thickness wound involves loss of the dermis and extends to deeper tissue layers and involves disruption of the dermal blood vessels. The healing of the partial thickness wound occurs by simple regeneration of epithelial tissue. Wound healing in full thickness wounds is more complex, involves multiple cell types (Martin, Science, 276:75–81 (1997)), and three stages. The first stage involves an immediate inflammatory response (2–5 days post wounding), followed by a proliferative phase (2 days–3 weeks) where no blood vessels (angiogenesis) and collagen are generated in the wound bed, resulting in the formation of granulation tissue. Contraction and re-epithelialization of the wound also occur during this phase. Finally, a maturation phase occurs during which collagen in the wound is subject to turnover and remodeling, ultimately resulting in the formation of scar tissue.

Intact epidermis serves as a mechanical barrier to infection. Due to the extensive tissue loss or damage in full thickness wounds, infection of more likely than in partial thickness injuries. Not properly cleaned and treated, a full thickness wound may, in severe cases, result in the development of a life-threatening infection.

A large number of dressings, bandages, and topic medicaments are available for the treatment of wounds. These products fall into two categories, passive and active. Passive wound dressings are dressing which serve only to provide mechanical protection and a barrier to infection. The dressings themselves do not supply any composition which enables or facilitates the healing process of the wound. Examples of passive dressings include gauze and adhesive bandages. Active dressings are dressing which supply some biologically active compound to the site of a wound. One type of active dressing is a dressing or wrapping which delivers or has been impregnated with antimicrobials (e.g., Bacitracin).

Another family of dressings which contain both passive and active properties are the hydrogels or hydrocolloids. Although many of these dressings do not supply any biologically active compound to the wound, they are specifically designed to create a moist environment around the wound to promote wound healing. Hydrogel and hydrocolloid dressings have been formulated to antimicrobials to help prevent and/or treat infection. However, to date, hydrogels or hydrocolloids have not been formulated with components that actively promote wound healing.

It has been suggested that the topical application of biological compounds may play an active role in wound healing. These compounds include mitogens, cytokines, growth factors, and hormones (e.g., PDGF, EGF, β-FGF, GM-CSF, IGF-I, TGF-α, and TGF-β). However, there are limitations to these therapies. First, it is difficult to regulate the dosage of such an application. A liquid or viscous paste containing these components applied to a wound will tend to spread away from the site of the wound, or will be absorbed by and removed from the wound by dressings which are placed over the wound. Dressings which come in contact with the wound surface may also interfere with the normal healing process. Furthermore, these compounds are all polypeptides, they are extremely susceptible to rapid degradation following there application. Such degradation can occur from the contact of the polypeptides with proteases produced by bacteria normally on the surface of the skin. In addition, these agents may lack specificity in there action, and have adverse pleiotropic effects on adjacent tissues other than those tissues involved in wound healing.

In some cases, abnormal wound healing represents a significant health risk to patients. In particular, diabetic patients often experience slow and/or incomplete wound healing that may result in other serious consequences. Diabetes mellitus (DM) is a metabolic disease resulting from defective glucose utilization. A variety of molecular defects are implicated in the manifestation of type-I and type-II diabetes, including errors in insulin production, glucose transport, and glucose metabolism (Nathan, Scientific American Medicine (Dale and Federman, EDS.), Chapter 9, Section VI (1997)). Both type-I and type-II DM produce a variety of debilitating and life threatening complications, including degeneration of large and small blood vessels (i.e., macrovascular and microvascular disease) and increased susceptibility to infection. These two complications, unfortunately, make the DM patient prone to poor wound healing and wound infections. In extreme cases, limb amputation is necessary due to circulatory problems and infection at the site of wounds.

It has been proposed that insulin can be administered systemically or topically to help promote wound healing in diabetic and normal patients. The results described in the literature have been fairly inconsistent. Some studies have found that the topical application of insulin helps to promote wound healing (Hanam et al., The Journal of Foot Surgery, 22:298–301 (1983)) and others have found no significant effect by insulin on the rate of wound healing, particularly in decubitus ulcers (Gerber and VanOrt, Nursing Research, 28:16–19 (1979)). Two U.S. Pat. Nos. 5,145,679 and 5,591,709 have described the topical administration of insulin to a wound to promote wound healing. Both of these patents, however, describe the use of insulin in combination with glucose because the function of the insulin is to enhance the uptake of glucose and to thus promote wound healing.

SUMMARY OF THE INVENTION

The invention provides improved methods and compositions for promoting wound healing. In particular, the invention involves the use of cyanoacrylate polymer sealants in combination with therapeutics, such as silver and insulin, and related compositions. Cyanoacrylate polymers have previously been used to form sealants to close holes in tissue, or to replace or supplement sutures or as a hemostat. The cyanoacrylate can be applied to the skin as a liquid or gel to produce a protective barrier film. Although the prior art has suggested the use of cyanoacrylates alone, or sometimes in combination with antimicrobials (U.S. Pat. No. 6,001,345) the prior art has been limited. Prior patents have shown that most medications alter the performance of cyanoacrylates, either preventing them from setting or causing them to set so rapidly that they cannot be used to form protective films, see e.g. U.S. Pat. No. 5,684,042. Additionally, the prior art suggested that protein based medicaments could be expected to be inactivated by the protein binding properties of cyanoacrylates. The methods and products of the invention have overcome many of these prior art problems. In particular, a new way for formulating cyanoacrylate compositions to incorporate biologically active molecules has been discovered according to the invention.

In some aspects, the invention relates to a composition of a cyanoacrylate polymer sealant and silver and/or insulin incorporated within the cyanoacrylate polymer sealant. The silver and insulin retain biological activity even when formulated within the cyanoacrylate polymer sealant. The composition, even though formulated with biologically active agents, is capable of sealing tissue and promoting wound healing. In some embodiments, the composition includes insulin incorporated in the cyanoacrylate polymer, such that at least 50% of the insulin is biologically active. In other embodiments, at least 60, 65, 70, 75, 80, 85, 90, 95, 98, or 99% of the insulin is biologically active.

Preferably the cyanoacrylate polymer sealant is composed of a monomer which comprises a cyanoacrylate ester. In some embodiments, the cyanoacrylate ester is derived from a monomer having a side group alkyl chain consisting of 1–10 or 4–10 carbon atoms. In some embodiments, the alkyl chain is butyl, octyl, or decyl. A preferred alkyl chain is N-butyl. In yet other embodiments, the composition also includes a biocompatible plasticizer, such as, dioctyl phthalate. A polymerization inhibitor may also be added.

The silver incorporated within the cyanoacrylate polymer sealant may be any type of silver. For instance, the silver may be a sulfadiazene, a silver salt, or a solid metallic silver. In some embodiments, the solid metallic silver is colloidal silver. In other aspects, the invention relates to a method for enhancing wound healing by administering to a wound the composition of the cyanoacrylate polymer sealant having silver or insulin incorporated therein in an effective amount to enhance wound healing. In some embodiments, the silver is colloidal silver or metallic forms of silver. The metallic form is not restricted to any particular size or dimension or shape. Indeed, alternative forms of metallic silver are contemplated, including, but not limited to, such forms as microbeads, mesh, granules, grains, silver-coated fibers, or silver filings.

The invention further provides formulations in which additional reagents are used to supplement the polymerizable cyanoacrylate monomer and the silver or insulin. Such reagents may include solublization reagents, anti-polymerization reagents, pliability reagents, stabilization reagents, or any combination of these reagents.

In some embodiments, the composition is applied to the surface of the wound in a liquid formulation. In particularly preferred embodiments, at least one cyanoacrylate monomer and silver or insulin are combined and applied to a wound under conditions such that the cyanoacrylate monomer polymerizes and forms a cyanoacrylate-silver or insulin matrix over and within a wound. In still other embodiments of the methods, an additional step of monitoring the progress of wound healing is incorporated.

The invention in other aspects relates to a method for enhancing wound healing by administering to a wound an effective amount for enhancing wound healing for a cyanoacrylate polymer sealant and silver. In some embodiments, the silver is a silver mesh which may optionally be laid down directly over a wound and the cyanoacrylate is applied over the surface of the silver mesh under conditions such that the cyanoacrylate polymerizes. In other embodiments, the cyanoacrylate may be applied to the silver mesh in vitro and the cyanoacrylate/silver mesh may be applied or laid over the surface of the wound. In other embodiments, the silver is silver sutures and the sutures are used to close the wound and the cyanoacrylate is applied over the surface of the wound and sutures. In other embodiments dissimilar metals are used together, for instance, zinc and silver are used together.

In other embodiments of the method, a further step of applying a current across the silver to enhance flow into the wound is incorporated. The current may be applied using electrophoresis or any other method for applying current.

The method may also involve the application of insulin to the wound in addition to the silver. The insulin may be incorporated directly into the cyanoacrylate polymer sealant or, optionally, it may be injected directly into the wound or applied topically to the wound prior to the application of cyanoacrylate polymer sealant.

In yet other aspects, a method for reducing scar formation is provided. The method involves administering to a wound a cyanoacrylate polymer sealant and a compound selected from the group consisting of insulin and silver, wherein the combination of the sealant and the insulin or silver results in a synergistic reduction in scar formation. In some embodiments, insulin is administered directly to the wound. The direct administration may involve topical administration or injection. Optionally, the insulin may be incorporated in the cyanoacrylate polymer sealant. In other embodiments, the silver is administered directly to the wound. Alternatively, the silver may be incorporated in the cyanoacrylate polymer sealant.

In another aspect the invention is a method for enhancing wound healing in a hyperglycemic subject. The method involves administering to a wound a cyanoacrylate polymer sealant and a glucose antagonist in an effective amount for enhancing wound healing. In one embodiment the glucose antagonist is 2-deoxy glucose.

In yet another aspect the invention is a method for enhancing wound healing in a hypoglycemic subject. The method involves administering to a wound a cyanoacrylate polymer and a sugar in an effective amount for enhancing wound healing. In one embodiment the sugar is glucose.

In other aspects the invention relates to a method of preparing a cyanoacrylate adhesive containing a medicament. The method involves neutralizing or slightly acidifying the medicament, drying the solution, micronizing the medicament, and dissolved or suspending the medicament in the cyanoacrylate formulation. Preferably the medicament is insulin, a sugar, or a sugar antagonist. In one embodiment the medicament is adjusted to a pH of about 5–7.0 in solution. In other embodiments the moisture content is below 1000 ppm, and more preferably below 100 ppm.

In some embodiments the medicament is associated with a carrier such as sugars, polysaccharides or other biocompatible polymers such as polyvinyl pyrrolidone (PVP), sodium carboxymethyl cellulose (CMC) or gelatin. Optionally the medicament may be mixed into an aqueous solution of the carrier, wherein the amount of carrier is greater than the amount of medicament, bringing the solution to a pH between 5 and 7, and drying the solution. In one embodiment the carrier is a sugar oligomer such as trehalose.

In other aspects a composition prepared by the method described above is provided. In some embodiments the medicament is insulin.

Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF THE DRAWINGS

FIG. 1A depicts the cyanoacrylate monomer and FIG. 1B depicts the cyanoacrylate polymer repeating unit.

DETAILED DESCRIPTION OF THE INVENTION

The invention relates to compositions and methods for treating wounds. The compositions include cyanoacrylate polymer sealants having silver or insulin incorporated therein. It was discovered surprisingly according to the invention, that compositions of a sealant composed of a cyanoacrylate polymer having biologically active agents incorporated therein could be produced and still function as a sealant and retain the biological properties of the components incorporated in the matrix. The compositions were found to be particularly effective in wound healing. It is contemplated that the wound healing activity of the silver and/or insulin combined with the effects of wound sealing by the polymerization cyanoacrylate results in dramatically enhanced wound healing.

It is envisioned, according to the invention, that the compositions will find significant use in treating wounds, especially in the treatment of chronic wounds or wounds which are resistant to healing, such as those seen in patients with diabetes mellitus. In addition, it is contemplated that such compositions and methods will also find use in a surgical setting to promote the healing related to surgical incisions.

It is believed that the compositions of the invention show enhanced activity resulting from a combination of the mechanical protection afforded by the cyanoacrylate sealant, in combination with the sustained release of the components incorporated therein. In some embodiments, a liquid cyanoacrylate monomer with the silver or insulin is distributed evenly over the site of the wound. The monomer which is applied topically to the wound or surgical incision polymerizes under nontoxic and physiological conditions to form an antiadhesive-semipermiable membrane, and thus, the mechanical barrier. By delivering the silver and/or insulin within a cyanoacrylate polymer matrix, a sustained, slow release of the medicament is also achieved. It is noted, however, that an understanding of the mechanism by which the compositions promote enhanced wound healing is not necessary to practice the present invention.

Thus, in some aspects, the invention is a composition of a cyanoacrylate polymer sealant having incorporated within the sealant silver and/or insulin. Preferably, the silver and/or insulin is incorporated and distributed evenly throughout the sealant.

Figure 1:
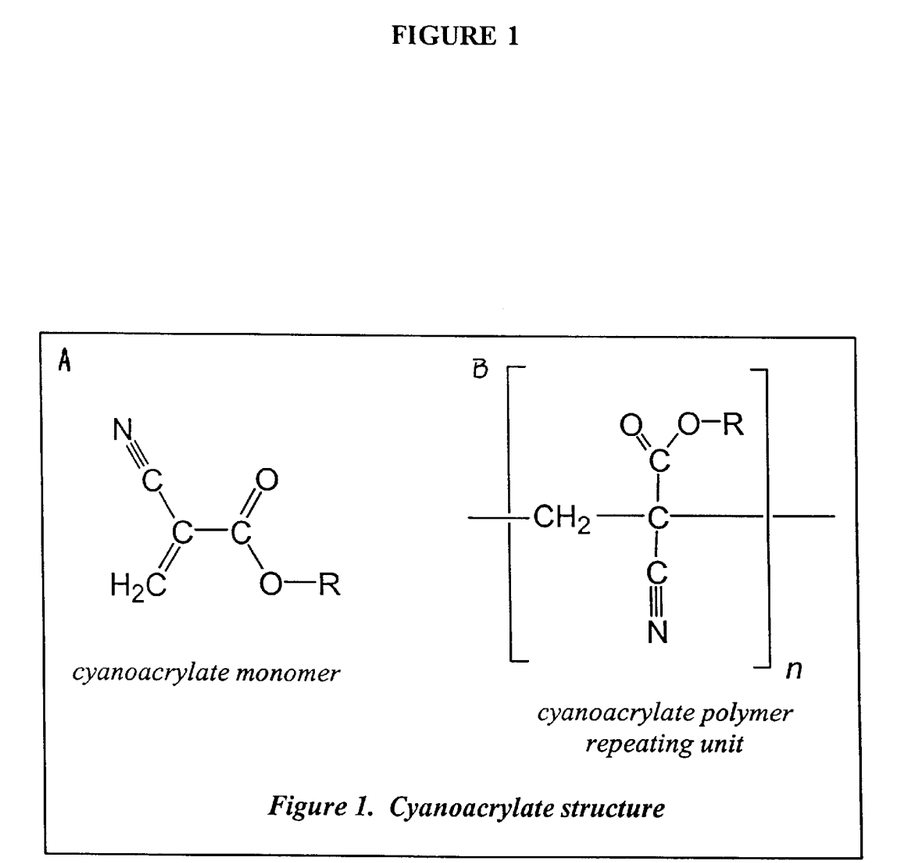
FIG. 1 shows the structure of cyanoacrylate.

Cyanoacrylate based adhesives have been described previously (see, e.g., U.S. Pat. Nos. 5,254,132; 6,001,345; and 6,102,205, each of which are incorporated by reference). The term "cyanoacrylate polymer sealant" refers to a polymeric formulation composed of cyanoacrylate monomers. Preferably, the cyanoacrylate monomer is a polymerizable cyanoacrylate ester, such as that shown in FIG. 1A. FIG. 1B shows the repeating unit of the polymerized form of the cyanoacrylate. Most preferably, R in formula in FIG. 1A is an alkyl group of from about 2 to 10 carbon atoms including ethyl, N-propyl, iso-propyl, N-butyl, iso-butyl, sec-butyl, N-pentyl, iso-pentyl, N-hexyl, iso-hexyl, 2-ethyl hexyl, N-heptyl, octyl, nonyl, and decyl. In preferred embodiments, R is N-butyl. The R group of the polymerized form of cyanoacrylate may be a mixture of such alkyl groups or each R group may be identical.

In order to optimize the incorporation of biologically active components into cyanoacrylate formulations the adhesive material may be prepared as follows. Cyanoacrylate monomers (prepolymers) may be polymerized by both anionic and free radical initiators and are therefore very sensitive to contaminants. Typically, basic contaminants will cause premature polymerization and acidic contaminants will prevent polymerization from occurring when it is desired. Even small amounts of water can be sufficient to cause premature polymerization if associated with mild bases such as soda glass. In addition, cyanoacrylates are known to bind to proteins when they polymerize, so that if a potentially bio-active component is protein based it will be permanently bound into the polymer matrix and effectively inactivated.

Incorporation of biologically active molecules into cyanoacrylate monomers may be accomplished by neutralizing or slightly acidifying the medicament to between pH 5 and 7.0 in solution and then thoroughly drying the solution. Preferably the moisture content will be below 1000 ppm, more preferably below 100 ppm. The medicament is then micronized and dissolved or suspended in the cyanoacrylate formulation. In the case of proteins or other medicaments containing amine derived groups, the activity may optionally be protected by entrapment in sugars, polysaccharides or other biocompatible polymers such as polyvinyl pyrrolidone (PVP), sodium carboxymethyl cellulose (CMC) or even gelatin. This may be achieved by mixing the active into an aqueous solution of the sugar or polymer containing more of the protectant than the active, bringing the solution to a pH between 5 and 7, and drying the solution. Of particular use in this method are sugar oligomers such as trehalose, which can protect the conformational structure of the protein on the absence of water.

Cyanoacrylate monomers can be polymerized under non-toxic, physiological conditions to form a polymer matrix with very strong bonding properties. The properties of the polymer may be controlled by the nature of the monomer side chain substituents, principally the ester moiety. A preferred cyanoacrylate ester is N-butyl-2-cyanoacrylate. The polymerizable cyanoacrylate esters rapid polymerize the presence of water vapor or tissue protein, and the cyanoacrylate bonds to human skin tissue without causing histotoxicity or cytotoxicity. Polymerizable cyanoacrylate esters have been described in the art in, for example, U.S. Pat. Nos. 3,527,224; 3,591,676; 3,667,472; 3,995,614; 4,035,334; and 4,650,826.

The cyanoacrylate compositions generally are prepared by polymerizing cyanoacrylate ester monomers under conditions which will allow for homogenous incorporation of the biologically active compound. In particular, the cyanoacrylate ester monomer is mixed thoroughly with the biologically active agent. It is important that the materials be a dry micronized powder. The material may be chilled or processed at room temperature.

The viscosity of the composition can be controlled during the preparation of the sealant. It is generally preferred to use a low viscosity sealant when the material is applied to a large surface area to allow for more even and consistent application to the area. When the application, however, is made to a smaller surface area a higher viscosity composition can be used in order to localize the sealant over the small area. In general, the composition has a viscosity of from about 2–50,000 centipoise at 20° C. The less viscous solutions are approximately 2–1,500 centipoise at 20° C. and the higher viscosity is approximately 2,000–50,000 centipoise at 20° C. In some preferred embodiments, the cyanoacrylate composition is almost entirely in monomeric form and the composition has a viscosity of from about 5–500 centipoise at 20° C.

In addition to the cyanoacrylate monomer and the biologically active agent, other components can be added to the composition. These include, for instance, a thickening agent, a biocompatible plasticizer, a polymerization inhibitor, and other pharmaceutically acceptable components and additives.

A "biocompatible plasticizer" is any material which is soluble or dispersible in the cyanoacrylate composition and which increases the flexibility of the polymer film coating on the skin surface. Plasticizers include, but are not limited to, those described in U.S. Pat. Nos. 2,784,127 and 4,444,933. Examples of specific plasticizers useful in the invention include, but are not limited to, acetyl, tri-N-butyl citrate, acetyl trihexyl citrate, butyl benxyl phthalate, dybutyl phthalate, dioctylphthalate, N-butyryl tri-N-hexyl citrate, diethylene glycol dibenzoate, etc.

Plasticizers are preferably included in the composition at from about 10–30 weight percent and more preferably at from about 18–24 weight percent based on the total weight of the composition.

A "polymerization inhibitor" as used herein is any material which is soluble or dispersible in the cyanoacrylate composition in which, in the amounts employed, inhibit the premature polymerization of the composition. Polymerization inhibitors are known in the art and include, but are not limited to, 4-methoxyphenol, sulfur dioxide, glacial acetic acid, and free radical inhibitors, such as hydroquinones.

A polymerization inhibitor is incorporated in the cyanoacrylate composition in an effective amount to inhibit premature polymerization in the composition. Preferably, the polymerization inhibitor is included in the composition at from about 50–1,000 PPM and more preferably from 100–500 PPM, based on the total weight of the composition.

A "thickening agent" as used herein is a compound which increases the viscosity of the composition. Thickening agents include, but are not limited to, polymethyl methacrylate (PMMA), and other preformed polymers and suspending agents, such as fumed silica. In general, fumed silica is useful for preparing a gel for topical application having a viscosity of approximately 1500–50,000 centipoise at 200° C.

Other components may be included in the composition including additives such as colorants, perfumes, rubber modifiers, and modifying agents.

The compositions of the invention include silver and/or insulin incorporated homogeneously throughout the cyanoacrylate polymer sealant. As described above, the silver and/or insulin is combined with an unpolymerized cyanoacrylate monomer to form homogenous suspension or solution. The material is then either polymerized and then added to the wound as a thin film or applied topically to the wound where it polymerizes. The result is a composition having a cyanoacrylate polymer matrix containing silver and/or insulin evenly distributed throughout. The entrapment of the silver and/or insulin within the cyanoacrylate provides a reservoir for slow controlled release of the silver to the wound. The rate of release or concentration of silver within the wound can be regulated by using various cyanoacrylate monomer forms as well as by varying the concentration of silver and/or insulin within the cyanoacrylate monomer prior to polymerization.

The silver useful according to the invention is any form of silver. One or more types of silver can be used to form the sealant. Thus, the composition may contain a single form of silver or multiple forms of silver. For instance, the silver may be, but is not limited to, ionic silver or solid metallic silver. As used herein, the term "silver" refers to various forms of silver, including solid or in solution. A "solublized silver salt" comprises dissolved ionic silver, indicated as "$Age^+$". As used herein, "ionic silver" does not have measurable length, width, height, weight, or diameter. "Metallic silver" is used in reference to the element silver in its solid form. Metallic silver may be manufactured to define physical dimensions, including specified length, width, height, weight, or diameter. Metallic silver encompasses colloidal silver. The colloidal silver protein (i.e., CSP) is at least one protein, complexed with elemental silver, in a manner such that the protein is rendered insoluble and forms a colloid when placed in a solution. As used herein, the term "salt" is any compound formed when the hydrogen of an acidic species is replaced by a metal (or other positively charged species). Most salts ionize (dissolve) in water. Examples of salts containing silver as the proton donor include silver nitrate and silver acetate. Ionic silver is generally utilized in the form of silver salt, e.g., silver nitrate, silver casein complex and silver pegylates (polyethylene glycol complexes). The invention also encompasses the use of molecular silver and high energy silver formed in plasmas or by vapor deposition.

Alternatively, a metallic form of silver may be incorporated in the cyanoacrylate matrix. As used herein "metallic silver" refers to a solid, pure form of element silver. In some embodiments, the metal silver is between 99.99% and 99.999% pure, although, silver of lesser purity may also be used according to the invention. Metallic silver may supplied as a colloid, in which the silver metal is a fine particle with the dimension of the particle being in the range between 1 and 100 nanometers, preferably. The dimension of the particle may be defined to be of any uniform size. Such colloidal silver solutions are commercially available (e.g., from Sauquoit Industries). As used herein, a "colloid" is particulate matter that is evenly distributed into a second substance (e.g., water). A colloid is not dissolved, but rather suspended evenly through a second substance, and is considered to be in a phase intermediate between a true solution and a suspension. The particles within a colloid will not settle by gravity. A solid particulate is defined as a colloid if one or more of the dimensions of the particle lie in the range between 1 and 100 nanometers. Colloidal silver is a colloid comprising elemental metallic silver.

Alternatively, the metallic silver may be of any size, shape or configuration. Such alternative forms of metallic silver may be termed, for example, mesh, shavings, granules, beads, fibers, or threads. It is noted that various manufacturers use different trade names for their silver products. Thus, it is not intended that the present invention be limited to any particular silver product produced by particular manufacturer. In addition, a silver bead from one commercial supplier may not have the same dimensions as a silver bead from a different manufacturer. However, it is not intended that the metallic silver used in the present invention and suspended in the unpolymerized cyanoacrylate monomer should be limited to any particular size or shape.

It is possible to modulate the wound healing characteristics of the compositions of the invention by modulating the nature of the metallic silver contained within the cyanoacrylate. For instance, a very small silver particulate may be effective for treating one type of wound, while a larger type of particulate metallic silver may be more effective for treating a different type of wound. The terms "modulate" as used herein refers to a change in biological activity of a biologically active molecule. Modulation can be an increase or a decrease in activity, a change in binding characteristic, or any other change in the biological function or properties of the biologically active molecules.

In another alternative embodiment, silver may be use in a pliable silver fiber or mesh form. Such fiber or mesh can be produced by depositing silver by various methods on a flexible scaffold such as nylon. Methods for depositing silver onto a surface include chemical deposition, electroplating, or vacuum deposition. Various silver coated fibers and meshes are commercially available (e.g., from Sauquiot Industries). In one embodiment, a piece of pliable silver mesh is cut to the approximate size of a wound, and is then placed over the wound. The cyanoacrylate monomer may then be placed over the mesh and allowed to polymerize. Once it polymerizes, the pliable silver mesh is incorporated in the cyanoacrylate and the cyanoacrylate affixes the silver directly over the wound. It is also possible to polymerize cyanoacrylate monomers around the silver mesh prior to placing the mesh over the wound. The polymerized mesh material can then be placed over the wound and sealed or held in place using conventional means. For instance, additional cyanoacrylate monomers can be applied to the surface of the polymerized material or the wound and once the polymerized cyanoacrylate/mesh material is placed over the wound, the unpolymerized material can be polymerized to seal the mesh to the wound.

The methods and compositions of the invention also encompass the use of insulin in combination with the cyanoacrylate polymer sealant. Insulin, as used herein, refers to any naturally occurring or recombinant mammalian insulin. Preferably, the insulin is naturally occurring or recombinant human insulin. Human insulin is a well known protein which is readily available commercially from a number of sources including, but not limited to, Sigma Chemical Company and Novo Nordisk. Naturally occurring human insulin is a protein having a molecular weight of approximately 5,500 daltons and includes approximately 51 amino acids. Depending on the manufacturer, the insulin may have slightly different activity based upon weight, however, the activity of insulin defined in units is the standard.

In additional to naturally occurring and recombinantly produced insulin, the term insulin according to the invention encompasses insulin analogs, including homologs and derivatives thereof from natural, synthetic, semi-synthetic and recombinant sources, as well as non-insulin hypoglycemic agents that have similar activities to insulin or which increase insulin receptors. Insulin having various degrees of biological activity is commercially available. For instance, it is possible to purchase low-, intermediate-, and rapid-acting forms of insulin. Non-insulin hypoglycemic agents that have similar activities to insulin or which increase insulin receptors include but are not limited to sulfonyl ureas (e.g., glibenclamide, gliclazide, glipizide, glyburide, chlorpropamide, tolbutamide, tolazamide, acetohexamide, and glimopride); thiazolidine diones (e.g., troglitazone and ploglitazone); α-glucosidase inhibitors (e.g., acarbose and miglitol); and third generation insulin-releasing agents (e.g., KAD 1220, etoxomir, and repaglinide).

The insulin is incorporated into the cyanoacrylate polymer sealant in an effective amount for promoting wound healing. The methods for preparing the cyanoacrylate polymer sealant/insulin composition allow for the incorporation of biologically active insulin into the sealant without effecting the sealant properties. Thus, in some embodiments, the insulin incorporated in the sealant is between 50 and 100% and every integer percentage there between, biologically active. In some embodiments, the composition includes approximately 0.0000005%—about 0.1% by weight insulin. The invention also encompasses a method for treating wounds and preventing scar formation by applying the insulin to the wound and subsequently applying the cyanoacrylate polymer sealant to the wound surface. The insulin could be injected directly into the wound or applied topically on the surface.

It has been discovered, surprisingly, according to the invention that the combination of insulin administered directly to the surface with the sealant administered directly over the insulin and without incorporating the insulin therein results in surprisingly beneficial effects on wound healing and scar formation. Although insulin had previously been used for wound healing, the results have been inconsistent in the literature. It was discovered, rather unexpectedly, according to the invention that the combination of insulin with the cyanoacrylate polymer sealant was significantly better than either component alone in enhancing and promoting wound healing. This was true even when the insulin was not incorporated within the cyanoacrylate polymer and effecting a slow release. Many of the prior art references describing the-administration of insulin to wounds during wound healing require multiple applications of insulin. The methods of the invention only require a single application of the insulin and then the wound is sealed with the cyanoacrylate. It is possible, however, according to the invention to apply multiple dosages of insulin, e.g., by injecting the insulin into the wound through the sealant. But multiple applications are not necessary because of the unexpected benefits achieved when the insulin was applied directly to the surface of the wound and then sealed with the cyanoacrylate polymer. It was also discovered that when glucose is used rather than insulin, the enhanced effects on wound healing were not observed. This was surprising because several references suggest that insulin functions by inducing glucose production locally. In some embodiments, the insulin is administered without any glucose.

In these aspects of the invention, the insulin can be applied to the wound in an effective amount for promoting wound healing. In general, concentrations of insulin will range from about 5 ng/ml to about 100 micrograms/ml. This amount corresponds generally to about 120 micro units/ml to about $24 \times 10^5$ micro units/ml. The actual amount will vary and may fall outside of these ranges, depending upon the wound treated, as well as other factors recognized by those of ordinary skill in the art.

The present invention provide improved methods of promoting wound healing and reducing scar formation. In particular, the cyanoacrylate polymers in combination with the silver and/or insulin provide vast improvements over the prior art method of promoting wound or reducing scar formation.

As used herein, the term "wound" is used throughout the specification to describe skin wounds which are treated by the formulations and the methods described herein as well as tissue wounds. A skin wound is defined herein as a break in the continuity of skin tissue which is caused by direct injury to the skin. Skin wounds are generally characterized by several classes including punctures, incisions, including those product by surgical procedures, excisions, lacerations, abrasions, atrophic skin, or necrotic wounds and burns. The compositions and methods of the invention are useful for enhancing the healing of all wounds of the skin.

A "tissue wound" as used herein is a wound to an internal organ, such as a blood vessel, intestine, colon, etc. The materials of the invention are useful for enhancing the wound healing process in tissue wounds whether they arise naturally or as the result of surgery. For instance, during the repair of arteries the vessel needs to be sealed and wound healing must be promoted as quickly as possible. The compositions of the invention can speed up that process. The compositions of the invention are also particularly useful for the treatment of damaged tissue in the colon. In addition to promoting the wound healing of the damaged colon, the silver can provide an antimicrobial effect.

As described above, the method for promoting wound healing may be accomplished by applying a cyanoacrylate polymer sealant incorporating silver and/or insulin therein directly to the wound. Alternatively, the method for promoting wound healing may involve the direct application of the silver and/or insulin to the surface of the wound prior to the application of cyanoacrylate polymer sealant. In some embodiments, the uptake of the biologically active component, e.g., insulin and/or silver or other component, can be enhanced using the application of an electric field. The electric field aids in the delivery of the biologically active component through the skin or material that has begun to form the scar. This method helps to continue the administration of the biologically active component even after the skin has begun to regenerate to repair the wound. This embodiment may be accomplished using electrophoresis and/or electroosmosis. Electrophoresis operates by having an electrode with the same charge as that of the ionic molecules above the solution adjacent to the skin which is the site of administration. The ions will be repelled and migrate through the skin and/or other tissue into the lower parts of the wound. Electroosmosis involves the use of a negative electrode causing an electric current to flow resulting in the movement of the biological active agents. One system for accomplishing this is described in U.S. Pat. Nos. 6,129,696, 4528265; 5,503,632; and 6,129,696 and PCT/US00/03304.

The methods of the invention are also useful for preventing scar formation. The compositions can be use to prevent the formation of a scar at the same time as promoting wound healing. Alternatively, the compositions may be used for preventing scar formation by reducing or initiating regression of existing scars. Scar tissue as used herein refers to the fiber rich formations arising from the union of opposing surfaces of a wound. It has been discovered according to the invention that the use of a combination of cyanoacrylate polymer sealant and insulin and/or silver results in a dramatic reduction in scar formation. The term "reduction in scar formation" as used herein refers to the production of a scar smaller in size than would ordinarily have occurred in the absence of the active components and/or a reduction in the size of an existing scar. The compositions administered for the reduction in scar formation can include a cyanoacrylate polymer sealant with the insulin and/or silver incorporated therein or the use of cyanoacrylate polymer sealant over top of insulin and/or silver which has been applied directly to the site of the scar formation.

The compositions and methods of the invention may also include additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetyl pyridinium chloride, antibiotics, and analgesics.

Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-α, TGF-β, cartilage inducing factors-A and -B, osteoid-inducing factors, osteogenin and other bone growth factors, collagen growth factors, heparin-binding growth factor-1 or -2, and/or their biologically active derivatives. The compositions may also include antiseptics.

It has also been discovered according to the invention that wound healing can be promoted in hypoglycemic and hyperglycemic subjects by combining the cyanoacrylate with a sugar or a sugar antagonist. It was discovered surprisingly in contrast to the findings observed in normal subjects (described above) the administration of sugar or sugar antagonists to hypoglycemic or hyperglycemic subjects had enhanced effects on wound healing when combined with cyanoacrylate. Thus, the invention includes a method for enhancing wound healing in a hyperglycemic subject by administering to a wound a cyanoacrylate polymer sealant and a glucose antagonist in an effective amount for enhancing wound healing. In some preferred embodiments the glucose antagonist is 2-deoxy glucose. A "hyperglycemic subject" as used herein is a subject that has an abnormal excess of sugar in the blood. A "glucose antagonist" is a compound which reduces the activity or availability of naturally occurring glucose when it is applied to the wound.

The invention also includes a method for enhancing wound healing in a hypoglycemic subject by administering to a wound a cyanoacrylate polymer and a sugar in an effective amount for enhancing wound healing. In one embodiment the sugar is glucose. A "hypoglycemic subject" as used herein is a subject that has an abnormal decrease of sugar in the blood.

When administered, the therapeutic compositions, such as insulin, silver, and/or other compounds such as antimicrobials, can be administered in pharmaceutically acceptable preparations. Such preparations may routinely contain pharmaceutically acceptable concentration of salt, buffering agents, preservatives, compatible carriers, supplementary therapeutic agents.

Preferably, the therapeutic agents are administered locally by topical application or injection. But the optional therapeutics may be administered by any conventional route including, for example, oral, pulmonary, intravenous, intraperitoneal, intrarectal, intraoccular, intramuscular, intracavity, subcutaneous, or transdermal. Those of skill in the art can readily determine the various parameters and conditions for producing these formulations without resort to undue experimentation.

The compositions are administered in effective amounts. An effective amount is that amount that alone or together with further doses or therapeutics produces the desired response, e.g., promoting wound healing or reducing scar formation. This amount may involve a slowing in the progression of scar formation although more preferably, it involves halting altogether the progression of scar formation. It also may involve only increasing the rate and degree of wound healing slightly or more dramatically. In some embodiments, the effective amount is an effective amount for promoting synergistic increase in wound healing or decrease in scar formation when compared to the administration of the cyanoacrylate polymer sealant or the insulin and/or silver alone. The actual amount delivered, of course, will depend upon the severity of the condition, the individual patient parameters, including age, physical condition, size, weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgement. It will be understood by those of ordinary skill in the art, however, that a patient may insist on a lower dose or tolerable dose for medical reasons, physiological reasons, or for virtually any other reasons.

The pharmaceutical compositions preferably are sterile for administration to a patient. When administered, the compositions are applied in pharmaceutically acceptable amounts and pharmaceutically acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but not pharmaceutically acceptable salts may conveniently be used to prepare pharmaceutically accept salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium, or calcium salts.

The term "pharmaceutically acceptable carrier" as used herein means one or more compatible solid or liquid fillers, diluents or encapsulating substances which are suitable for administration into the human or animal. The term "carrier" denotes an organic or inorganic ingredient, natural or synthetic, with which the active ingredient may be combined to facilitate the application.

The compositions of the invention are useful for promoting wound healing and reducing scar formation in a subject. As used herein, the term "subject" refers to a human or non-human animal, including, but not limited to, a cat, dog, horse, pig, cow, sheep, goat, rabbit, mouse, rat, or monkey.

EXAMPLES

Example 1

Use of a mouse model for full-thickness wound healing.

This examples describes the method for testing the efficiency of cyanoacrylate-silver and/or insulin composition in promoting wound healing. A full-thickness incisional model for wound healing is used. In this technique, a 4MM diameter segment of epidermis and underlying dermis is surgically removed from a shaved area on the back of an anesthetized mice. The wound is placed so that the mice cannot lick or chew the wound site. Wounded mice are individually caged. The wounds are given one of three interventions, including: (i) no treatment; (ii) treatment with cyanoacrylate alone; and (iii) treatment with cyanoacrylate co-polymerized with silver and/or insulin. Three mice are used in each group and each experiment, and the experiment is repeated a minimum of three times.

The rate of reepithelialization is followed by monitoring wound size. This is accomplished by tracing the outline of the wound onto a glass coverslip and measuring the resulting surface area of the outline.

Healing is likely to be complete by 5–7 days. At 7 days, post wounding, the mice are euthanized and the wound site harvested for preparation of tissue sections and histopathological examination. The histopathological examination of the wound site is used to determine the occurrence of cell division, inflammatory response, cell death and indications of healing.

In summary, the present invention provides advantages over the prior art, most notably in applying silver and/or insulin to the site of a wound in the controlled release manner using polymerized cyanoacrylate to provide wound healing activity and/or reduction in the scarring. It is contemplated that the invention will also find use in the treatment of wounds in persons with poor wound healing, including patients with diabetes mellitus. In general, the cyanoacrylate polymer sealant is formed around the wound by applying an cyanoacrylate ester composition to the intact skin surface peripheral to the wound and covering the wound. Preferably, the insulin and/or silver is incorporated within the cyanoacrylate ester composition. Once the monomers are subjected to contact with the surface skin moisture, tissue protein, etc., the material polymerizes in situ to form a cyanoacrylate polymer film.

The polymerization process occurs at ambient skin temperature, generally within seconds. The polymerization process usually is complete within about 10–100 seconds as long as the skin is maintained at ambient conditions. During that time period, it is preferred to limit patient movement to prevent dislodgment of the cyanoacrylate material. After polymerization, the polymeric film strongly adheres to the skin and is flexible and waterproof. Generally, the film is so adherent that the film will not separate from the patients skin until the wound has healed. After a period of about 1–4 days, the polymeric film sloughs off This occurs because the cyanoacrylate polymer only adheres to the upper most portion of the epidermal layer which is continually in the process of being sloughed off and replaced by the underlying cells. It is possible to apply additional layers of cyanoacrylate sealant after the first layer is polymerized. Additional layers, however, are not necessary. Preferably, the final polymeric film has a thickness of about 500 microns and preferably is less than 1 millimeter.

Example 2

In vivo determination of bonding time for tissue adhesive formulations.

Methods:

Twelve mice were used in the study. An incision of approximately 1 centimeter was made horizontally (perpendicular to the backbone) on the dorsal skin of the mouse. This is the control incision. A second horizontal incision is made on the other side of the backbone. The test cyanoacrylate was placed over the second incision. Both incisions are held together for approximately 30 seconds and then released. The mice were observed over a period of several days.

Two cyanoacrylate materials were formulated and tested. The first formulation included 2% F-68 (12% 12) polymer, a sample weight of 975 grams, a sample titrable iodine of 0.2%, a setting time (plate) of 10 seconds and a viscosity of 25 C:5.16cP. The second formulation included 6% F-68 (19.5% $I_2$) polymer, a sample weight of 971 grams, a sample titrable iodine of 0.81%, a setting time (plate) of 15 seconds, and a viscosity of 25 C:6.27cP.

Results

Results were collected from six mice having two incisions. The right side incision received cyanoacrylate alone and the left side incision on each animal received test cyanoacrylate. On the first mouse, the right side incision demonstrated some reaction to the product and a thicker scab indicating longer healing time. The left side of the same mouse had no reaction and a quicker healing time. The second mouse died before completion of the study and could not be analyzed. The third mouse showed some wound healing improvement on both incisions. The fourth mouse showed some irritation on the left side incision and a small area of irritation at the lower end of the right hand incision which was not due to infection. The fifth and sixth mouse showed wound healing with very little irritation.

Example 3

Effect of three day insulin treatment on unsealed wound in vivo.

Methods

Six mice were anesthetized with avetin Q 15–18 micro liters per gram body weight. An area on the back of the neck was swabbed with alcohol and shaved. A single vertical incision was made with scissors. One hundred micro liters of insulin was applied to three mice and 100 micro liters of water was applied to the other three. Photographs of the wounds were taken on a daily basis for one week.

Results

More complete wound healing was observed in mice tested with insulin as opposed to water. The effects were especially pronounced in later stages of the wound healing, possibly, because the levels of glucose are higher earlier on.

Example 4

Effect of three day insulin and glucose treatments on unsealed wounds in vivo.

Methods

The methods were performed as described above except that twelve mice were used; three of the mice were administered sterile water; three of the mice were administered 4 milligrams per milliliter of insulin (40 micro liters stock plus 960 micro liters of water); three mice were administered 30 millimolar glucose (300 micro liters of stock plus 700 micro liters of water); and three mice were administered insulin and glucose. On day 0, each animal was administered 25 micro liters of the treatment solution. The treatment was repeated on days 1 and 2. Photographs were taken every other day and blood glucose levels were measured.

Results

On day 4 of treatment, there was no observable differences in the rate of healing with any of the treatments as compared with the control mice. By day 7, there was no significant difference in the rate of healing of the wounds and all of the wounds were improving, but slowly.

Example 5

Effect of glucose and insulin treatments on blood glucose level and rate of wound healing when combined with cyanoacrylate.

Methods

Twelve mice were used in the study. Each mouses' blood glucose level was tested at the start of the study. The mice were then weighted and anesthetized. The back of the neck was shaved and a single incision was made. The incision was then sealed with cyanoacrylate polymer which was applied and allowed to set for 1½ minutes. The treatment (glucose, water, insulin, or insulin plus glucose) as described above were injected into the incision. Blood glucose levels were measured at 30 minutes and again at 3½ hours. On day 1, blood glucose was again measured and the wound was photographed. This was repeated on days 3, 5, and 7. Mouse numbers 1, 2, and 3 received glucose treatment. Mouse numbers 4, 5, and 6 received water (control). Mouse numbers 7, 8, and 9 received insulin plus glucose. Mouse numbers 10, 11, and 12 received insulin.

Results

The results of the blood glucose measurements for each of the twelve mice is set forth in Table 1. As shown in Table 1, glucose treatment did not have any significant effect over that of control water treatment. Insulin plus glucose and insulin alone had dramatic effects in the levels of blood glucose.

TABLE 1

| | | Blood Glucose Level (mg/dL) | | | |
|---|---|---|---|---|---|
| M# | Treatment | 0 Hr | 0.5 Hr | 3.0 Hr. | 21 Hr. | 69 Hr. |
| 1 | Glucose | 111 | 105 | 81 | 95 | 96 |
| 2 | Glucose | 105 | 122 | 82 | 91 | 105 |
| 3 | Glucose | 108 | 121 | 84 | 75 | 96 |
| 4 | Water (Control) | 109 | 54 | 80 | 58 | 86 |
| 5 | Water (Control) | 108 | 125 | 103 | 79 | 121* |
| 6 | Water (Control) | 83 | 77 | 83 | 81 | Died |
| 7 | Insulin + Glucose | 115 | 47 | <25 | <25 | 81 |
| 8 | Insulin + Glucose | 104 | 27 | <25 | <25 | 79 |
| 9 | Insulin + Glucose | 104 | <25 | <25 | <25 | 95 |
| 10 | Insulin | 89 | 58 | <25 | <25 | <25* |
| 11 | Insulin | 104 | 36 | <25 | 113 | 109 |
| 12 | Insulin | 118 | 46 | <25 | <25 | Died |

*Died by 10/23/00

The foregoing written specification is considered to sufficient to enable one skilled in the art to practice the invention. The present invention is not limited in scope by the examples provided, since the examples are intended as illustrations of various aspects of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. All references, patents, and patent publications that are recited in this application are incorporated in their entirety herein by reference.

We claim:

1. A method for enhancing wound healing, comprising:
   administering to a wound an effective amount for enhancing wound healing of a cyanoacrylate polymer sealant and silver, wherein the silver is a silver mesh.
2. The method of claim 1, wherein the silver mesh is applied to the surface of the wound and the cyanoacrylate is applied over the surface of silver mesh.
3. The method of claim 1, wherein the cyanoacrylate is applied to the silver mesh and the cyanoacrylate/silver mesh is applied to the surface of the wound.
4. A method for enhancing wound healing, comprising:
   administering to a wound an effective amount for enhancing wound healing of a cyanoacrylate polymer sealant and silver, wherein the silver is silver sutures.
5. A method for enhancing wound healing, comprising:
   administering to a wound an effective amount for enhancing wound healing of a cyanoacrylate polymer sealant and silver, further comprising applying a current across the silver to enhance flow into the wound.
6. The method of claim 5, wherein the current is applied using electrophoresis.
7. A composition, comprising:
   a cyanoacrylate polymer sealant and insulin, the insulin incorporated within the cyanoacrylate polymer sealant, and wherein at least 50% of the insulin is biologically active.
8. The composition of claim 7, wherein at least 80% of the insulin is biologically active.
9. The composition of claim 7, wherein at least 90% of the insulin is biologically active.
10. The composition of claim 7, wherein at least 95% of the insulin is biologically active.
11. The composition of claim 7, wherein the cyanoacrylate polymer sealant is composed of a monomer which comprises a cyanoacrylate ester.
12. The composition of claim 11, wherein the cyanoacrylate ester is derived from a monomer having a side group alkyl chain consisting of 1 to 10 carbon atoms.
13. The composition of claim 7, further comprising silver incorporated in the cyanoacrylate polymer sealant.
14. A method for enhancing wound healing, comprising:
    administering to a wound the composition of claim 7 in an effective amount for enhancing wound healing.
15. The method of claim 14, wherein the composition is applied to the surface of the wound in a liquid formulation.
16. The method of claim 14, further comprising the step of monitoring the progress of wound healing.
17. A method for reducing scar formation, comprising:
    administering to a wound a cyanoacrylate polymer sealant and a compound selected from the group consisting of insulin and silver, wherein the combination of the sealant and the insulin or silver results in a synergistic reduction in scar formation.
18. The method of claim 17, wherein the compound is insulin.
19. The method of claim 18, wherein the insulin is administered directly to the wound.
20. The method of claim 19, wherein the insulin is administered topically to the wound.
21. The method of claim 19, wherein the insulin is injected into the wound.
22. The method of claim 18, wherein the insulin is incorporated in the cyanoacrylate polymer sealant.
23. The method of claim 17, wherein the compound is silver.
24. The method of claim 23, wherein the silver is administered directly to the wound.
25. The method of claim 23, wherein the silver is incorporated in the cyanoacrylate polymer sealant.
26. A method for enhancing wound healing, comprising:
    administering to a wound an effective amount for enhancing wound healing of a cyanoacrylate polymer sealant and silver, wherein insulin is incorporated into the cyanoacrylate polymer sealant.
27. A method for enhancing wound healing, comprising:
    administering to a wound an effective amount for enhancing wound healing of a cyanoacrylate polymer sealant and silver, further comprising contacting the wound with insulin.
28. The method of claim 27, wherein the insulin is injected into the wound.
29. The method of claim 27, wherein the insulin is applied topically to the wound.

* * * * *